United States Patent [19]

Morris et al.

[11] Patent Number: 5,571,800
[45] Date of Patent: Nov. 5, 1996

[54] METHOD FOR INHIBITING ALLOGRAFT REJECTION BY THE ADMINISTRATION OF 6-AZAURIDINE OR ITS TRIACETATE DERIVATIVE

[75] Inventors: Randall E. Morris, Los Altos; Robert I. Fox, La Jolla; William Drell, San Diego, all of Calif.

[73] Assignee: Azura, Inc., Carson, Nev.

[21] Appl. No.: 330,510

[22] Filed: Feb. 14, 1994

Related U.S. Application Data

[63] Continuation-in-part of Ser. No. 63,010, May 17, 1993, abandoned.

[51] Int. Cl.$^6$ ............................................. A61K 31/70
[52] U.S. Cl. ............................ 514/50; 514/49; 514/885
[58] Field of Search ................................ 514/49, 50, 885

[56] References Cited

U.S. PATENT DOCUMENTS

5,023,083  6/1991  Drell ........................................ 424/439
5,200,400  6/1993  Teramoto et al. ......................... 514/45

OTHER PUBLICATIONS

American College of Rheumatology, 46th Annual Scientific Meeting, Atlanto, Georgia, Abstract Reproduction Form, cover sheet, 2–3, Table 1–3 (Oct. 1992).

Chen et al., "Mechanism of Action of the Novel Anticancer Agent 6–Fluoro–2' (2'–fluoro–1,1'–biphenyl–4–yl) –3–methyl–4–quinolinecarboxylic Acid Sodium Salt (NSC 368390): Inhibition of de Novo Pyrimidine Nucleotide Biosynthesis," Cancer Research 46 5014–5019 (Oct. 1986).

Drell, William, "Azaribine–Homocystinemia–Thrombosis in Historical Perspective", Pharmac. Ther., 41 195–206 (1989).

Elis et al., "Side Effects of 6–Azauridine Triacetate in Rheumatoid Arthritis," Clinical Pharmocology and Therapeutics, St. Louis, 11(3) 404–407, (May 1970).

Fischer et al., "Immunosuppression by Pyrimidine Nucleoside Analogs," Biochem. Pharmacol. 15 1013 (1966).

Havelka et al., "6–Azauridin–Triacetat in der Therapie de Chronischen Polyarthritis," Sonderdruck aus Zeitschrift für Rheumaforschung, 28(1/2) 29–35 (Jan./Feb. 1969).

Mathies, H., 109871p "Treatment of Rheumatic Illnesses with Immunosuppressive Substances," 15—Pharmacodynamics, Chemical Abstracts 74 230 (1971).

Raskova et al., 1435t "Unexpected Side–Effects of 6–Azauridine in Rheumatoid Arthritis and Feedback in Animal Experiments," Chemical Abstracts 77 60–61 (1972).

Sutton et al., "Drug Effects on Survival of Homografts of Skins," Archives of Surgery, pp. 840–843, vol. 87, Nov. 1963.

Primary Examiner—James O. Wilson
Attorney, Agent, or Firm—Christie, Parker & Hale, LLP

[57] ABSTRACT

A method for suppressing the rejection of an allograft comprising administering azaribine at a time when the recipient of the allograft begins to mount a reject reaction against the allograft.

3 Claims, No Drawings

METHOD FOR INHIBITING ALLOGRAFT REJECTION BY THE ADMINISTRATION OF 6-AZAURIDINE OR ITS TRIACETATE DERIVATIVE

RELATED APPLICATIONS

The present application is a continuation in part of U.S. patent application Ser. No. 08/063,010 filed May 17, 1993, now abandoned, which is incorporated herein by reference.

FIELD OF THE INVENTION

The present invention relates to a method for suppressing acute rejection after organ transplantation, even after the rejection reaction has been initiated.

BACKGROUND OF THE INVENTION

Although transplantation of organs is becoming commonplace, rejection of the donated organ by the patient remains a serious problem. Almost all transplant recipients require an immunosuppressive regimen to prevent such rejection. However, immunosuppressive drugs also suppress the body's defenses against infection. Thus, transplantation requires a continuous effort to induce acceptance of the graft without paralyzing the body's immune system and without the additional stress of undesirable side effects produced by the immunosuppressive drug itself.

When an allograft, such as kidney, liver or heart, is transferred from one mammal across a strong histocompatibility barrier to another, the allograft is initially vascularized and the recipient's immune cells begin to proliferate. After about 10 days the allograft becomes the site of intense inflammation and the allograft is infiltrated by lymphocytes which leads to the rejection of the tissue. This type of rejection reaction is due primarily to the action of T-lymphocytes or the cell-mediated immune response of the recipient host to the allograft.

In mammals, precursors of active T-lymphocytes are activated by their contact with an antigen. After contact, the lymphocytes enlarge, enter into the mitotic cycle, proliferate and acquire specific cytolytic activity. Suppression of rejection is usually directed at preventing the T-lymphocytes from proliferating.

A typical regimen for immunosuppression, starting before or at the time that the transplantation is performed comprises one or more of the following agents or therapies: (1) corticosteroids, such as prednisone or prednisolone; (2) inhibitors of nucleic acid synthesis, such as azathioprine, cyclophosphamide and mycophenolic acid; (3) T-cell inhibitors, such as cyclosporin and FK-506; (4) therapies such as x-ray irradiation; and (5) polyclonal and monoclonal anti-lymphocyte and antithymocyte antibodies.

All of these therapy methods have undesirable side effects. Many transplant recipients face serious infection from opportunistic organisms including bacteria, fungi, protozoa and viruses. Some types of cancer are as much as 100 times more frequent in transplant recipients. The corticosteroids may additionally cause diabetes mellitus, osteoporosis and cataracts. The cytotoxic agents may cause anemia, hypertension, thrombocytopenia and damage to the liver and bladder. Cyclosporin may cause decreased renal function, hypertension and undesirable effects on the central nervous system.

Acute rejection may respond or is prevented by currently available immunosuppressive agents. Clinical manifestations of acute renal transplant rejection may include fever, graft swelling or tenderness, oliguria, and increases in blood urea nitrogen (BUN) and serum creatinine levels. Rejection of a transplanted liver or heart leads to the loss of the important metabolic and cardiovascular functions of these organs.

It is desirable that a composition, and method of use of such a composition is developed, which is effective when administered after the rejection reaction (described above) has been initiated. Such administration avoids unnecessary treatment if a rejection reaction to a transplanted organ is delayed or does not develop. The ability to postpone treatment minimizes the side effects of the immunosuppressive agent by reducing the overall period of time required for treatment, or enables new treatments to be initiated when a previously used treatment has not been effective.

SUMMARY OF THE INVENTION

A method for suppressing the rejection of an allograft comprising administering azaribine or 6-azauridine at a time when the recipient of the allograft begins to mount a rejection reaction to the allograft, preferably within 6 days after surgery. In a preferred embodiment of the present invention the azaribine is administered orally at a dosage of about 35 to about 600 milligrams per kilogram of body weight, per day. In another embodiment of the present invention 6-azauridine is administered parenterally at a dosage of about 25 to about 500 milligrams per kilogram of body weight, per day.

DETAILED DESCRIPTION

6-Azauridine, and particularly its "orally effective" triacetate derivative, azaribine, has been found useful suppressing the immune system and thereby suppressing the rejection reaction using a heart transplant model. 6-Azauridine is thought to exert its biological activity by inhibiting orotidine-5'-phosphate decarboxylase, thereby reducing the availability of uridine and cytidine. Since uridine and cytidine are essential components for the synthesis of nucleic acids, their absence leads to an inability of immune lymphoid cells to proliferate and grow in response to the allograft. Therefore treatment with 6-azauridine or azaribine commenced prior to or immediately following transplant surgery will suppress the immune response that leads to tissue rejection. 6-Azauridine has been found to be a relatively safe drug compared to other cytotoxic agents. Doses up to 1,000 mg/kg/day have been administered to patients for up to 10 days with only transient side effects, which disappeared promptly on discontinuing drug therapy. In one study, no side effects were observed at doses of 600 mg/kg/day for 10 days [Weiss et al. *Cancer Chemotherap. Repts.* 53, 79–82 (1969)]. In another study, therapy at 400 mg/kg/day of azaribine has been employed for treating psoriasis and psoriatic arthritis [Levene et al., *Arth. Rheum.* 19, 21–28 (1976)]. The principal side effect, namely anemia, was ameliorated by reducing or discontinuing therapy. No side effects such as renal, cardiac or liver damage, which are common with other immunosuppressants, have been observed with azaribine.

The present invention is directed to the use of azaribine to suppress ongoing tissue rejection. The term azaribine as used herein refers to 2', 3', 5'-triacetyl-6-azauridine, also called 6-azauridine triacetate. This compound is metabolized to 6-azauridine in vivo. In the method of the present invention, 6-azauridine or azaribine is administered after the initiation of the rejection reaction to suppress the rejection of a transplanted organ or tissue. Preferably azaribine is administered orally at a dosage of about 35 to about 600 milligrams per kilogram of body weight, per day. Alternatively, parenteral administration of 6-azauridine at a dosage of about 25 to about 500 milligrams per kilogram of body weight, per day may be used. In the practice of the present invention, in the event that an ineffective agent has been earlier employed, 6-azauridine can be administered after initiation of the rejection reaction is observed.

In cases where the patient is unable to tolerate oral medication, intravenous injection of 6-azauridine is preferred.

The method according to the present invention includes an initial waiting period between transplantation of the allograft and administration of the immunosuppressing compound to determine if administration of the immunosuppressing compound is in fact required. This waiting period is typically between 2 and 4 days, but not more than 6 days.

General transplantation techniques for the kidney, the heart, the liver, skin and other organs and tissues are well known by those skilled in the art. In the examples given below, heterotrophic heart transplants were performed in mice. The heterotrophic heart transplant model has been used for more than twenty years as a model for the effectiveness of immunosuppressive drugs in humans. Milom et al., *Arch Path* 21, 281–287 (1971), Bahany et al., *J. Pharm & Exp. Therap.* 244, 259–262 (1988), Morris et al., *Transplant Proc.* 21 1042–1044 (1989), Morris et al., *Transplant Proc.* 22 1059–1652 (1990), Yuh et al., *Transplantation* 55 578–591 (1993). Human clinical trial cannot be performed until the effectiveness of a drug has been demonstrated in an established animal model. One of the reasons for this is to establish that the drug is not toxic. In the case of 6-azauridine, the drug has been used extensively for other conditions and treatments. The drug has been established as non toxic in humans even at very high doses, up to 1,000 mg/kg/day, Slavick et al., *Pharm. Clinica* 2 120–125 (1970), Levine et al., *Arthritis & Rheumatation,* 14 21–28 (1976), Weiss et al., *Cancer Chemo. Reports* 53 79–82 (1969). Mice are used as a model in immunology since their histocompatible genes are understood to a greater extent than any other mammal. A heterotrophic transplant than other mammals is used in these studies since there is no possibility that the transplanted tissue is compatible with the host. If the transplanted tissue were from an animal of the same strain the effectiveness of the immunosuppressant drug, would be inconclusive since the tissue transplanted could have been compatible with the host rather than the immunosuppressive drug being effective. To have a conclusive determination of the effectiveness of a drug heterotrophic transplants must be used. Such experiments cannot be performed in humans as such experimentation is unethical and prohibited by governmental regulations. The procedure accepted by those skilled in the art to test the effectiveness of a drug for human use, is to test the drug in an established animal model. Established animal models are considered to be predictive of the effects of drugs in humans.

In the present invention it is preferred that oral administration of azaribine is used. It is further preferred that the azaribine be administered in a formulation which is resistant to absorption by the stomach. A preferred chemical formulation comprises a generally solid composition containing azaribine which is then encapsulated in an enteric coating as disclosed in U.S. Pat. No. 5,023,083, which is incorporated herein by reference. The formulation may be orally administered in tablet, capsule, suspension or other suitable form. It is understood that other methods of administrations such as oral administration of non-enteric coated azaribine or intravenous administration of 6-azauridine, may be used as desired.

In the practice of the present invention, it is desirable that administration of the azaribine or its equivalent is initially at a high dosage, i.e. about 600 milligrams per kilogram of body weight, per day for azaribine and about 500 milligrams per kilogram of body weight, per day for 6-azauridine, to maximize suppression of the rejection reaction. However, undesirable side effects may develop at high doses of azaribine or 6-azauridine. If side effects develop the dosage is reduced to a level where the side effects are reduced or eliminated.

The effectiveness of the treatment of rejection of a transplanted tissue or organ with azaribine, at a time after the rejection reaction has been initiated, allows a reduction in the amount of drug which is to be administered. In addition the treatment does not have to be initiated as a preventative measure, instead, treatment can be withheld until needed, i.e. if the initial treament fails. Thus the treatment may be initiated when other medications have been tried and found to be ineffective. With some conventional treatments, if the treatments are not initiated prior to the onset of the rejection reaction they will not be effective.

Since it is believed that azaribine acts to inhibit nucleic acid synthesis, it is unexpected that azaribine would be effective in suppressing the ongoing rejection reaction, i.e. after the rejection reaction has been initiated. After the rejection reaction has begun the T-cell population would have already undergone cell proliferation and growth. Therefore, nucleic acid synthesis would no longer be essential for the rejection reaction to proceed and presumably would no longer be affected by nucleic acid synthesis. The rejection reaction would presumably be unaffected by a nucleic acid synthesis inhibitor.

An experimental model system has been developed which correlates the immunosuppressive activity of a drug in the mammal (mouse) with its anticipated activity in human organ transplants [Babany, et al., *J. Pharmacol. Exp. Therap.* 244, 259–262 (1988)]. Such correlations exist with respect to cyclosporin, FK 506 [Morris, et al., *Transplant. Proc.* 2 1042–1044 (1989)], mycophenolic acid [Morris et al., *Transplant. Proc.* 22, 1659–1662 (1990)] and 15-deoxyspergualin [Yuh et al., *Transplant.* 55, 578–591 (1993); Amemiya, *Ann. NY Acad Sciences* 685, 196–202 (1993)].

The procedure is as follows: Following implantation of neonatal hearts, derived from unsexed newborn BALB/c mice, 24–48 hr. old into subcutaneous pouches prepared in the pinna of the ears of the recipients, male C3H/km mice 5–10 weeks old, heart grafts are examined for contractions every other day from day 4 to the final day of the experiment after surgery. In such transplantation procedures, the transplanted heart quickly becomes vascularized and begins to contract. About 4 days after transplantation, immune cells infiltrate the allograft and by day 6 infiltration is very advanced. Milam et al. [*Arch. Path.* 21, 281–287 (1971)] have shown that by day 8 untreated allografts are revascularized and infiltrated with polymorphonuclear leukocytes and by day 12, the interstitial infiltration and myocardial necrosis is extensive. By day 14 no control hearts are contracting. The success rate of the immunosuppressive drug is expressed as the mean survival time in days after transplantation. In all groups, all hearts are contracting by day 6. The length of graft survival time increases with increasing dosage of an effective immunosuppressive drug. The onset of rejection is marked by an increase in the body temperature of the recipient, infiltration of immune cells, inflammation, and in the case of the allografts described above the implanted heart ceases to contract. The onset of rejection is well known by those skilled in the art and such indicators are constantly monitored in transplant recipients. Some of clinical manifestations of rejection include fever, graft swelling or tenderness, oliguria, and increases in BUN and serum creatinine levels. Any of these indicators can be monitored to indicate the onset of rejection. Suppression of rejection is a reversal of these conditions after administration of the immunosuppressive drug.

EXAMPLE 1

The procedure described above was carried out with 5 mice housed in a single cage. On the day after transplantation, azaribine was dissolved in their drinking water at a concentration of 0.5 mg/ml. The volume consumed by the mice was recorded daily. After 14 days the azaribine-containing water was replaced by water which contained no additions. The mice were then observed daily for rejection of the allografts. The results are summarized in Table I.

EXAMPLE 2

The procedure described in Example 1 was repeated except the administration of 0.5 mg/ml azaribine, in drinking water, was commenced the second day after transplantation. The results are summarized in Table I.

EXAMPLE 3

The procedure described in Example 1 was repeated except the administration of 0.5 mg/ml azaribine, in drinking water, was continued for 30 days after transplantation. The results are summarized in Table I.

EXAMPLE 4

The procedure described in Example 1 was repeated except azaribine at a concentration of 0.75 mg/ml was administered in drinking water. The results are summarized in Table I.

EXAMPLE 5

The procedure described in Example 1 was repeated except azaribine at a concentration of 1 mg/ml was administered in drinking water. The results are summarized in Table I.

EXAMPLE 6

The procedure described in Example 1 was repeated except azaribine at a concentration of 1 mg/ml was administered in drinking water and the administration was continued for 23 days after transplantation. The results are summarized in Table I.

EXAMPLE 7

The procedure described in Example 1 was repeated except azaribine at a concentration of 1 mg/ml was administered in drinking water and the administration was commenced four days after transplantation and was continued for 13 days after transplantation. The results are summarized in Table I.

EXAMPLE 8

The procedure described in Example 1 was repeated except four mice were given azaribine at a concentration of 1 mg/ml of drinking water and the administration was commenced six days after transplantation and was continued for 13 days after transplantation. The results are summarized in Table I.

EXAMPLE 9

The procedure described in Example 1 was repeated except four mice were given azaribine at a concentration of 2 mg/ml in drinking water and the administration was continued for 13 days after transplantation. The results are summarized in Table I.

EXAMPLE 10

The procedure described in Example 1 was repeated except the administration of azaribine (1 mg/ml) was combined with 0.08 mg/ml cyclosporin A and the administration was continued for 13 days. The results are summarized in Table I.

EXAMPLE 11

The procedure described in Example 1 was repeated except the administration of azaribine (1 mg/ml) was combined with 1 mg/ml mycophenolic acid and the administration was continued for 13 days. The results are summarized in Table I.

The results indicate that the administration of azaribine at a dosage of between about 97 mg/kg to about 320 mg/kg is effective in suppressing the rejection of an allograft, with the mean survival time being increased from about 10 to 12 days to about 18 days. The survival was increased even when treatment was not commenced until 4 or 6 days after transplantation. Typically, rejection is already initiated by day 4 and is usually very advanced by day 6. The delayed treatment had little or no effect on the mean survival time. The addition of cyclosporin or mycophenolic acid did not affect the mean rejection times.

The above description of exemplary embodiments for the use of azaribine in immunosuppression are for illustrative purposes. Variations which will be apparent to those skilled in the art, therefore, the present invention is not intended to be limited to the particular embodiments described above. Also, the invention disclosed herein may be practiced in the absence of any element which is not specifically disclosed in the specification. The scope of the invention is defined by the following claims.

TABLE I

| Example | Drug | Dose[1] | Schedule[2] | ml/mouse[3] | mg/mouse[4] | mg/kg[5] | Mean[6] | SEM[7] | N[8] |
|---|---|---|---|---|---|---|---|---|---|
| 1 | AZARIBINE | 0.5 | 1–14 | 5.8 | 2.9 | 103.0 | 17.3 | 0.7 | 5 |
| 2 | AZARIBINE | 0.5 | 2–14 | 5.5 | 2.75 | 101.0 | 17.5 | 0.5 | 5 |
| 3 | AZARIBINE | 0.5 | 1–30 | 5.3 | 2.63 | 97.0 | 18.5 | 0.5 | 5 |
| 4 | AZARIBINE | 0.75 | 1–14 | 5.2 | 3.9 | 139.0 | 18.0 | 0.6 | 5 |

TABLE I-continued

| Example | Drug | Dose[1] | Schedule[2] | ml/mouse[3] | mg/mouse[4] | mg/kg[5] | Mean[6] | SEM[7] | N[8] |
|---|---|---|---|---|---|---|---|---|---|
| 5 | AZARIBINE | 1 | 1–14 | 4.2 | 4.2 | 147.0 | 18.4 | 0.7 | 5 |
| 6 | AZARIBINE | 1 | 1–23 | 4.4 | 4.4 | 169 | 24.4 | 0.4 | 5 |
| 7 | AZARIBINE | 1 | 4–13 | 5 | 5 | 188.0 | 15.6 | 0.4 | 5 |
| 8 | AZARIBINE | 1 | 6–13 | 5.2 | 5.2 | 190.0 | 17.5 | 1.5 | 4 |
| 9 | AZARIBINE | 2 | 1–13 | 4 | 8 | 320 | 19.0 | 2.3 | 4 |
| 10 | AZA[9]/CSA[10] | 1/0.08* | 1–13 | 4.6 | 4.6 | 162.0 | 18.8 | 0.8 | 5 |
| 11 | AZA/MYCO[11] | 1/1* | 1–13 | 4.8 | 4.8 | 166.0 | 18.4 | 1.0 | 5 |

[1] mg/ml in drinking water
[2] indicates the day, after transplantation, treatment was started–and ended
[3] ml of drinking water consumed per mouse per day
[4] mg of drug consumed per mouse per day
[5] mg of drug consumed per kg of body weight per day
[6] mean survival time of the allograft, in days, after transplantation
[7] standard error of the mean
[8] number of mice per test
[9] azaribine
[10] cyclosporin A
[11] mycophenolic acid
[12] mg/ml

What is claimed is:

1. A method for suppressing the rejection of an allograft in a mammal comprising the administering of a therapeutic dose of azaribine or 6-azauridine at a time after the recipient of the allograft has begun to mount a reject reaction against the allograft.

2. A method for suppressing the rejection of an allograft as recited in claim 1 wherein azaribine is administered orally at a dosage of 35 to 600 milligrams per kilogram of body weight, per day.

3. A method for suppressing the rejection of an allograft as recited in claim 1 wherein 6-azauridine is administered parenterally at a dosage of 25 to 500 milligrams per kilogram of body weight, per day.

* * * * *